United States Patent [19]

Feng

[11] 4,011,472
[45] Mar. 8, 1977

[54] ACOUSTIC EMISSION TRANSDUCER
[75] Inventor: Ching C. Feng, San Clemente, Calif.
[73] Assignee: Becton, Dickinson Electronics Company, San Juan Capistrano, Calif.
[22] Filed: May 13, 1975
[21] Appl. No.: 577,035
[52] U.S. Cl. .................................. 310/8.1; 73/558; 310/8.2; 310/8.3; 310/9.1; 310/9; 333/72
[51] Int. Cl.² ........................................ H01L 41/04
[58] Field of Search ............. 310/8.1, 8.2, 8.3, 8.4, 310/8.6, 9.1, 9.4, 9.2, 9.3, 9, 8.9; 73/88.5, DIG. 1, DIG. 4, 557, 558, 559, 69, 70, 71, 71.5 US; 340/8 R, 8 FT, 8 LF, 9, 10, 15.5 CP; 333/72

[56] References Cited
UNITED STATES PATENTS

| | | | |
|---|---|---|---|
| 3,031,528 | 4/1962 | Bolston | 73/558 |
| 3,284,763 | 11/1966 | Burg et al. | 340/15.5 MC |
| 3,400,783 | 9/1968 | Lee et al. | 340/15.5 CP |
| 3,582,691 | 6/1971 | Sonderegger et al. | 310/8.4 |
| 3,700,937 | 10/1972 | Rissolo | 310/8.3 X |

Primary Examiner—Mark O. Budd
Attorney, Agent, or Firm—Reed C. Lawlor

[57] ABSTRACT

The electromechanical acoustic emission detector of this invention comprises a plurality of sensor elements secured in an areal array on a base plate. The spacing and arrangement of the sensor elements are such that the transducer is "tuned" to acoustic emission waves that travel along the surface of the vessel to which the transducer is attached. Because of the non-linear character of the array the transducer detects waves arriving from different directions with substantially equal sensitivity.

15 Claims, 7 Drawing Figures

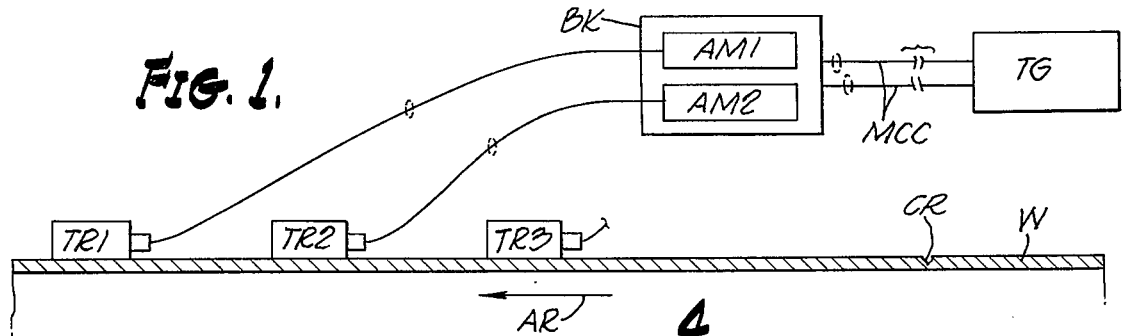
FIG. 1.
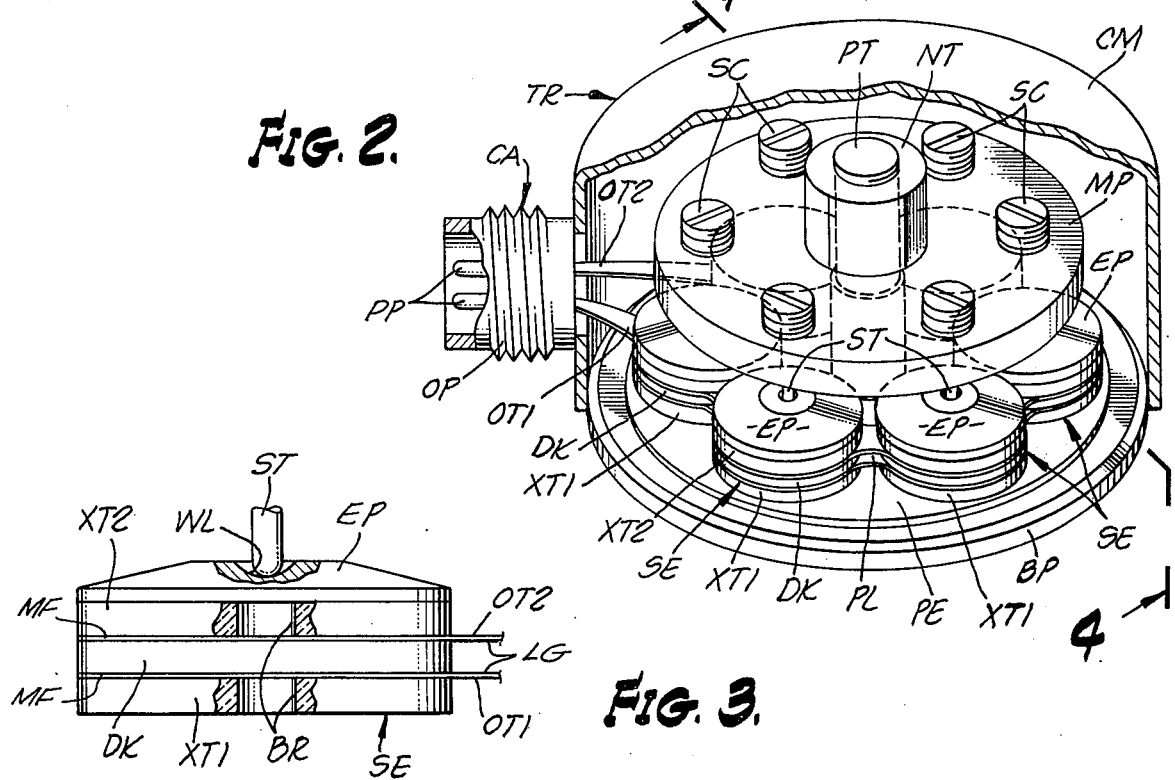
FIG. 2.
FIG. 3.
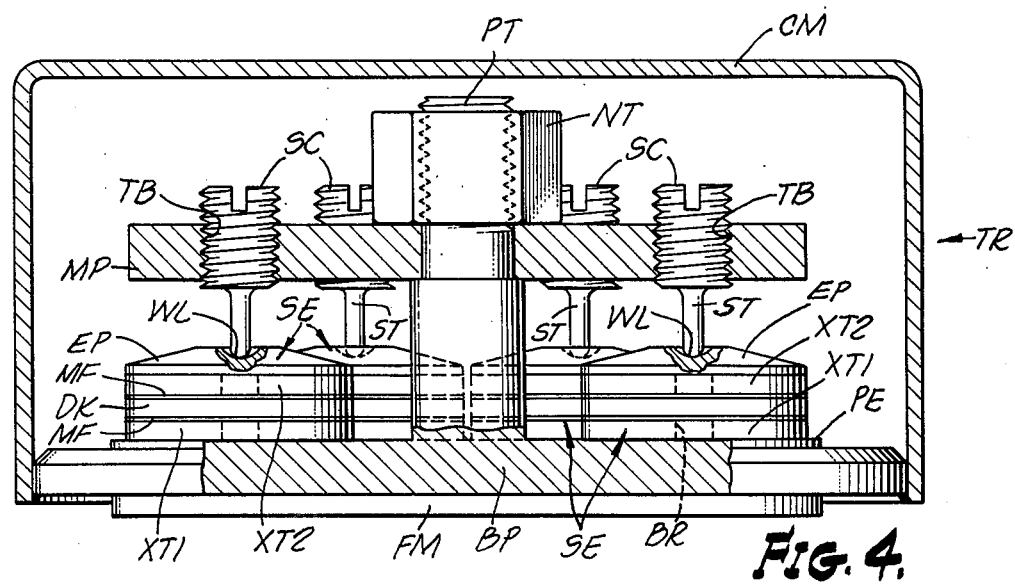
FIG. 4.

ACOUSTIC EMISSION TRANSDUCER

This invention is concerned with improvements in electromechanical acoustic emission detectors, or transducers, for detecting acoustic emission signals that are emitted by solid objects, such as by cracking, and converting them to electrical signals having components of corresponding frequency.

BACKGROUND

Acoustic emission, to which the present invention particularly applies, is concerned with the detection of elastic waves that are emitted from a source within an object and become manifest at positions remote from the source. Acoustic emission signals are also emitted from various points of an object spontaneously at various times. Often acoustic emission occurs as a result of growth of cracks. Such cracks may arise from the application of various kinds of forces to the object such as mechanical pressure or because of temperature changes or even chemical action.

By way of example, vessels employed in refineries emit acoustic signals often when they are subjected to increasing pressure. Rocket motors, or at least prototypes thereof, are often tested in advance of use by subjecting them to increasing pressure thereby generating acoustic emission signals. Acoustic emission may also arise spontaneously from unidentified causes while an object is standing apparently undisturbed.

The location of cracks and other sources of acoustic emission has been determined for many years by locating acoustic emission detectors at various points on the surface of the object under investigation, detecting the signals received and the relative times of arrival thereof at the respective detectors, and then either manually or automatically calculating the origin of the acoustic emission signals by triangulation or similar methods, taking into account the relative times of arrival of waves at the detectors and the propagation speed of the waves. The severity of the phenomenon, such as cracking, that accounts for the acoustic emission, has been determined by observing the strength of the waves arriving at the detectors such as by counting the number of pulses or groups of pulses detected in a given interval of time or over an extended time.

Many other signals that occur simultaneously constitute noise and therefore, if also detected, may obscure the acoustic emission phenomenon under investigation. Various methods have been employed for improving the signal-to-noise ratio. This invention is concerned with a new type of acoustic emission transducer for selectively detecting acoustic emission signals in a predetermined high frequency band in preference to other signals.

GENERAL DESCRIPTION

This invention is based in part on the recognition of the fact that acoustic emission signals, though traveling in a direction parallel to the surface of the object, often consists in part of waves which have components of displacement, velocity and acceleration that are transverse to the surface and are of short wavelength. While such a wave travels along the surface, at any one point on the surface it has a component that moves back and forth along a path that is transverse to the surface. Though such waves also have other components, such transverse components are here often referred to simply as transverse waves. Thus, except for the fact that they are traveling in a solid and are of small amplitude, the waves have an undulatory or sinuous component like the waves on the sea. Like the waves of the sea, in effect, the transverse acoustic emission signals are characterized by a wavelength which depends upon the frequency of the signals and the wave speed.

Surface waves include Rayleigh waves, which predominate among the surface waves that travel in thick walls. They also include Lamb waves, which are predominant in the surface waves that travel in thin walls. Both Rayleigh waves and Lamb waves have components that are transverse, or perpendicular, to the surface. For this purpose, a wall is considered thick or thin depending upon whether or not its thickness dimension exceeds approximately 3 wavelengths of the wave under consideration.

GENERAL STATEMENT OF THE INVENTION

It has long been recognized that in many environments, noise masks acoustic emission signals at frequencies below about 100 kHz, and also above about 1200 kHz. Below about 100 kHz the masking is due primarily to noise of a mechanical nature.

At high frequencies above about 1200 kHz, the acoustic emission signals themselves are very weak, largely because the attenuation of the acoustic emission signals that travel in the surface of the vessel increases by about the fourth power of the frequency.

The main purpose of this invention therefore, is to provide an acoustic emission transducer that is selectively responsive to transverse surface waves in such predetermined high frequency range lying between about 100 kHz and 1200 kHz.

It has been found that detectors having a maximum sensitivity between 300 kHz to about 600 kHz are especially effective for the detection of transverse acoustic signals characteristic of acoustic emission in the walls of vessels. Advantage is taken of this fact in this invention by providing a multiple sensor acoustic emission transducer that has an area of contact with the surface of the wall that has a maximum dimension that is a low non-zero integral multiple of the wavelength of acoustic emission signals in that range, that is a wavelength of about 0.27 inch.

In accordance with this invention a multiple sensor transducer is provided, that has a maximum sensitivity to transverse surface waves traveling in a solid object over a broad band of frequencies lying between about 100 kHz and about 1200 kHz, and which is sensitive to acoustic emission signals arriving at the transducer from any direction along the surface of the object under study. In the best embodiment of the invention such a transducer comprises six cylindrical piezoelectric sensors arranged in a circle on a common base plate and the individual piezoelectric sensors are designed to have a radial resonant frequency in the same high frequency range. The piezoelectric sensors are of substantially equal sensitivity and the radius of the circle in which they are arranged is "tuned" to the wavelength of acoustic emission signals in the predetermined broad range.

As will be seen hereinafter, one such radius is about 1.15 times the wavelength in question. The corresponding frequency is sometimes referred to as the "resonant frequency" of the transducer and the coresponding wavelength as the "resonant wavelength".

The sensor elements may be of any form in which mechanical forces applied to the elements in a direction normal to the surface of the object are converted to electrical signals of corresponding amplitude and frequency. By virtue of the fact that the sensor elements are arranged over an area, as in a circle rather than in linear fashion, the transducer responds to signals arriving from different directions with substantially the same sensitivity.

The base plate on which the sensors are mounted is relatively thin so that when it is cemented to the surface of the object various parts of the base plate partake of the same transverse surface motion as points on the surface of the object. The outputs of the electromechanical sensors are interconnected electrically, such as by connecting them in parallel, so that a combined electrical signal is produced that represents the sum of the signals arriving simultaneously at the points of the surface of the object directly beneath the respective sensor elements. It is largely because of this fact that the transducer is tuned to signals having frequencies in the desired band.

The surface waves arriving at the various transducers arrive there in different time-phase relations so that some of the signals tend to reinforce each other and some tend to counteract each other. Maximum sensitivity of the combined signals occurs at a frequency that has a wavelength about equal to the radius of the circle.

The six piezoelectric sensor elements themselves have diameters almost equal to the radius of the circle on which their centers are arranged so that in effect, they extend over a substantial area of the base plate. For this and other reasons the response of the multisensor detector of this invention is not very sharp but extends over a broad frequency band that includes the resonant frequency.

It is not necessary to employ six piezoelectric sensors and it is not necessary for all the sensors to have the same sensitivity. And it is not necessary for the sensors to be arranged equiangularly, or equilaterally, in a circle. The invention may be carried out by employing three or more sensors arranged on a base plate in a non-linear array and arranging the spacing and interconnections between the outputs of the sensors in such a way that the combined electrical signals have their maximum sensitivity in the predetermined high frequency range.

The piezoelectric sensors of this invention are housed in a common case and are mounted in a novel way to facilitate precompressing the crystals individually by predetermined amounts to assure response to both downward and upward motions.

DESCRIPTION OF THE DRAWINGS

The invention as described herein with reference to the accompanying drawings wherein:

FIG. 1 is a combined schematic and block diagram illustrating an application of the invention;

FIG. 2 is a partially exploded isometric view of the transducer of this invention;

FIG. 3 is a cross-sectional view of a sensor employed in this invention;

FIG. 4 is a cross-sectional view of the transducer of FIG. 2 taken along the plane 4—4;

DETAILED DESCRIPTION OF THE INVENTION

In FIG. 1 there is illustrated schematically an arrangement of a plurality of acoustic emission transducers TR1, TR2, and TR3, etc. mounted on the exterior surface of the wall W of a pressurized vessel being investigated. The transducers are described as if their axes of sensitivity were vertical.

Figure 5:
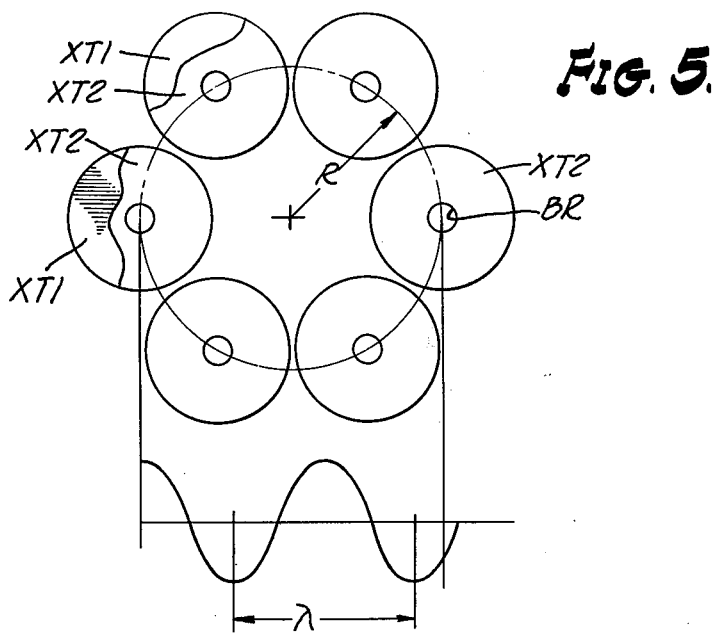
FIG. 5 is a diagrammatic plan view of the sensor arrangement.
Figure 6:
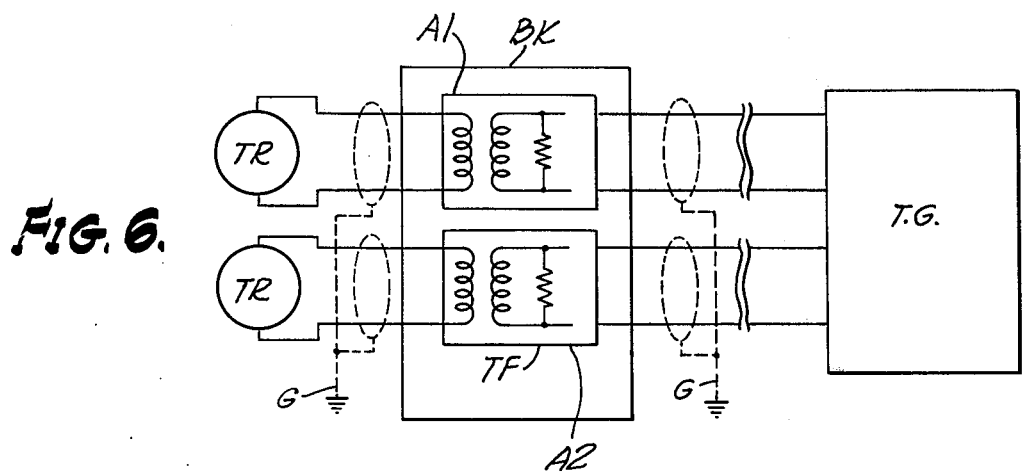
FIG. 6 is a more detailed wiring diagram illustrating the general nature of the electrical equipment employed with transducers of this invention.

Each of the transducers includes a plurality of electromechanical sensor elements arranged to be selectively responsive to transverse acoustic emission signals traveling along the surface of the wall W in a direction indicated by the arrow AR. In practice a large number of transducers may be employed, such as twelve and up, and as indicated in FIGS. 1 and 6 their electrical outputs may be supplied to a corresponding number of amplifiers AM, such as amplifiers AM1, AM2, etc., mounted in a bank BK adjacent the vessel and these outputs may be connected by means of a multiple conductor cable MCC to a utilization device such as a triangulation computer TG as a remote point. This invention is concerned with the transducers TR1, TR2, etc. that may be employed with amplifiers AM and utilization equipment TG of various kinds which are already well known in the art.

As indicated particularly in FIGS. 2, 3, and 4, an acoustic emission transducer of this invention may comprise six electromechanical sensor elements SE secured to a flat base plate BP. Each of the sensor elements SE is provided in effect, with a pair of output terminals OT1 and OT2. In effect all the sensor elements have their outputs connected in parallel as illustrated at PL in FIG. 2.

A cover member or case CM in the form of an inverted cup is welded to the base plate BP to protect the sensors from exposure to atmospheric or other ambient gases. An electrical connector CA having an outer tubular part OP and two pins PP that are mutually insulated from each other and from the base member and cover member, projects radially from the housing member CM. The output terminals OT1 and OT2 are connected electrically to the respective terminals P of the connector CA.

The outer tubular part OP of the connector CA may be threaded to receive a cable fitting or it may be welded directly to the sheath of a shielded cable.

A foot member FM in the form of an alumina disk is secured to the lower surface of the base plate BP and the acoustic emission transducers TR are mounted in place on the outer surface of the wall W by cementing the foot member FM to the surface of the wall.

The housings of the transducers are electrically connected to the outer sheaths of the shielded cables and the sheaths are connected to the system ground G.

As further indicated in FIGS. 2, 3, and 4, each of the electromechanical sensor elements includes two piezoelectric crystals XT1 and XT2 and an alumina disk DK sandwiched between them. The crystals XT1, XT2, and the disk DK are stacked under compression between the base plate BP and a mounting plate MP. The two crystals XT and the annular disks DK are of circular cylindrical configuration of substantially the same radius. Each of the crystals XT, namely crystals XT1 and XT2 is of annular configuration having a small bore BR at the center thereof for a special purpose that will be explained hereinafter. The flat surfaces of the two crystals have metal coatings deposited thereon such as by evaporation or chemical deposition and the cylindrical surfaces of the crystals are free of metal.

The alumina disk DK acts as an insulator between the crystals and also as a resilient member. The lower face of the lower crystal XT1 is in direct electrical contact with the base plate BP and the upper face of the upper crystal is electrically connected to cap or mounting plate MP. Thin sheets of metal foil MF having lugs LG radially extending therefrom, are arranged between the respective crystals and the central alumina disk DK to provide output terminals OT1 and OT2. For this purpose a single sheet of metal foil is employed on the opposite sides of the alumina disk DK, each sheet being cut to provide circular segments that match the crystals XT and the disk DK of each stack and the lugs LG that form straps that bridge the adjacent circular segments. The outer surfaces of the crystals are electrically connected together through the metal base plate BP, the metal cap or mounting plate MP, and other interconnecting metal structural members of the transducer. Thus the two crystals are electrically connected in series between the two output terminals OT1 and OT2.

The respective sensor elements are held securely in place by means of mounting screws having thin stems ST that press into the bottoms of shallow wells WL at the centers of the mount-end plates EP. The mounting structure includes a post PT that is unitary with the base plate BP at the center of the circular array of sensor elements and a circular mounting plate MP that is held in place by a nut NT. The mounting plate is provided with six threaded bores TB arranged directly above the stacks of crystals and the screws SC are adjustable vertically therein.

The threaded ends of the screws engage mating threads in the mounting plate. As a result, the mounting screws SC may be individually adjusted to apply pressure to the respective stacks. These screws precompress the sensor elements so that they are made responsive to both upward motion and downward motion of the respective parts of the base plate directly beneath the sensor elements over an extended range of movement.

The two crystals XTI and XT2 of each sensor are arranged with their polarization, or sensitive, axes parallel to each other and perpendicular to the base plate BP. With this arrangement, the electrical signals produced in the respective crystals of a stack as a result of the movement of the base plate toward and away from the mounting plate MP are added together electrically between the output terminals OT1 and OT2. Each of the sensors thus acts as a differential transducer with a grounded center and produces signals of substantially equal but opposite amplitudes at the output terminals OT1 and OT2.

In a multiple sensor transducer that has been found to be effective for selectably detecting acoustic emission signals in the predetermined frequency range mentioned, the six crystals have been uniformly spaced in a circle having a diameter of 0.5 inch so that the centers of the adjacent sensor elements are 0.25 inch apart. The crystals themselves and the insulators associated with them have diameters that are slightly less than this, being in practice about 0.24 inch in diameter so that the various sensors are mechanically isolated from each other except through the metal base plate and the metal mounting plate and the interconnecting metal support structure.

Each crystal has a thickness of 0.025 inch. The central alumina disc has a thickness of 0.020 inch. The metal foils have a thickness of 0.003 inch.

The base plate has a diameter of 0.94 inch, and a thickness of 0.10 inch. The diameter of the alumina foot member FM is about 0.80 inch, and its thickness is about 0.020 inch. A thin pedestal PE having a thickness of 0.010 inch is formed in the upper part of the base plate BP.

The upper surface of this pedestal is ground and polished flat to provide a flat surface upon which to mount the crystals. The various support structures including the foot member FM, the base plate BP, the pedestal PE, the central post PT, and the mounting plate MP are arranged coaxially within the case member CM and the lower end of the case overlaps the edge of the base plate by an amount less than the thickness of the alumina foot FT. The mounting screws MS and the nut NT are locked into place with locking cement to firmly hold the various parts together and the case CM is welded to the base plate BP.

Materials suitable for use as piezoelectric elements include polarizable ceramic polycrystalline materials and also natural piezoelectric crystals. Such ceramic materials include barium titanate, lead zirconate, lead metaniobate, bismuth titanate, and mixtures thereof with each other or with other suitable materials. Natural crystals suitable for use in the invention include quartz and lithium niobate. When the device is employed at high temperatures above 200° C, the piezoelectric materials typically have low dielectric constants of about 30 to 300. When employed at low temperatures, such as 20° C, the piezoelectric materials typically have relatively high dielectric constants of about 100 to 3000.

It can be shown that the peak response of a circular crystal array occurs at wavelengths $\lambda$ given by the solutions to the following equations:

$$X = \tan X \qquad 1.$$
$$\lambda = 4\pi R/X \qquad 2.$$

where
$R$ = radius of the circle
$\lambda$ = wavelength
$X$ = a parameter that interrelates R and $\lambda$ It can be shown that equation (1) has many solutions including $$X = 0, 1.43\ \pi, 3.47\ \pi, \text{etc.}$$

which for convenience are referred to as the first, second, third, etc. integral solutions.

In this invention, a solution value of X is employed which provides a radius that is a small integral non-zero multiple of the wavelength $\lambda_m$ near the center of the band of signals to be detected. If a large multiple is employed, many resonant frequencies appear in the band and the radius of the array becomes unnecessarily large. By employing too small a value of X the transducer becomes excessively smaller.

In the particular embodiment of the invention, the third solution, $3.47\ \pi$, is employed to determine the wavelength $\lambda_m$ to which the transducer is "tuned". This corresponds to a wavelength of 0.288 inch for a Rayleigh wave in steel having the propagation speed of $12 \times 10^4$ inches/sec so that the resonant frequency is 410 kHz. This is near the center of the predetermined frequency band and requires that the transducer have a diameter of only about 1 inch.

The wavelength $\lambda_m$ of maximum sensitivity calculated this way applies to a theoretical case in which the sensors have radii that are very small compared with the radius of the circle in which they are arranged. Thus, the calculation neglects the fact that each of the sensors contacts the base plate over an extended area thereof. This expansive contact results in a broadening of the response so that the multiple sensor transducer of this invention responds to a broad band of signals having wavelengths that includes the calculated value $\lambda_m$.

The sensitivity of the transducer is also broadened by the resonance characteristics of the crystals. In this connection it will be evident that the crystals have an axial vibration mode characterized by an axial resonance and a radial vibration mode characterized by a radial resonance and that these are coupled to the vibration mode of the array of sensors on the base plate because of the elastic properties of the crystal and Poisson-ratio relations. With the structures disclosed, the axial resonant frequency lies above 1200 kHz and the principal resonant frequency of interest is the radial resonant frequency. It can be shown that this latter frequency $f$ is given approximately by the following formula:

$$f = v/\pi(OR + IR)$$

Thus the radial resonant frequency depends upon the wave speed $v$, the outer radius OR, and the inner radius IR of the annulus. By way of example, for a crystal composed primarily of bismuth titanate and having an outer radius of 0.120 inch and an inner radius of 0.020 inch, the principal radial resonant frequency can be shown to be about 360 kHz.

The radial resonant frequency of the crystals is deliberately made different from the resonant frequency of the transducer as a whole corresponding to the resonant wavelength $\lambda_m$ by no more than between about ±10% and about ±20%. In this way the transducer is detuned somewhat, so as to enhance the broad-band frequency response without introducing two sharp peak responses of maximum sensitivity corresponding to the different resonant frequencies.

There are additional resonances in the system which lie outside the frequency band of maximum sensitivity or are otherwise immaterial. One of these is the resonant frequency of the crystal stack considered as an accelerometer with respect to vibrations parallel to its axis, that is, as a device in which the stack is a compliant member and the end plate EP acts as an inertia member. This resonant frequency is very low, being of the order of a few thousand cycles per second.

The outputs of the respective sensors are connected to the corresponding amplifiers AM in the bank BK of preamplifiers. Each of these amplifiers is provided with an impedance matching transformer TF at its input.

In practice, the amplifiers AM and the remainder of the system to which the multiple sensor transducers are connected have transmission characteristics that selectively amplify signals in the predetermined frequency range. As a result of the combined action of the entire system, the signal-to-noise ratio is enhanced in the predetermined frequency range.

In some instances, it is desirable to locate the preamplifier a substantial distance from the vessel undergoing tests. In this case, the transformers are mounted close to the vessel under test, and are connected to the amplifiers through long cables.

The transducers of this invention are employed for detecting transverse acoustic waves that travel along a wall W of a vessel from a source of acoustic emission signals. Such a source is exemplified by a crack CR (see FIG. 1) that is growing while the vessel is subject to pressure. The transducers of this invention are tuned to wavelengths where the signal-to-noise ratio of the transverse surface waves due to acoustic emission is high compared with background noise. For this purpose, as explained, the transducers are designed to have a resonant frequency that lies near the center of a band extending from about 100 kHz to about 1200 kHz.

Figure 7:
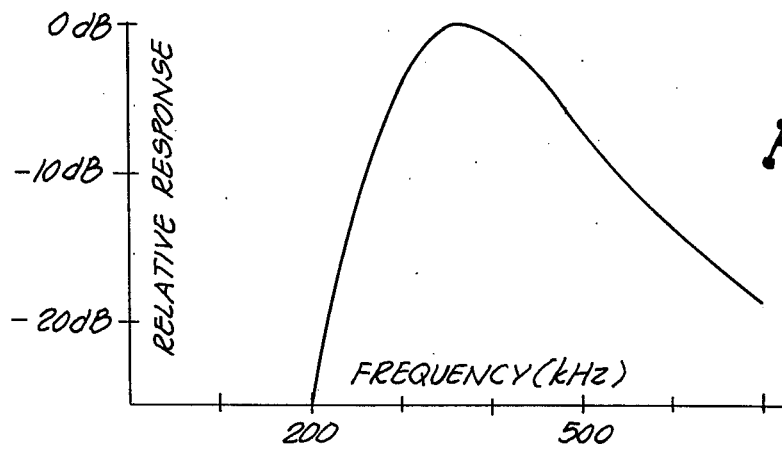
FIG. 7 is a graph representing the frequency response attained with this invention.

In FIG. 7, a graph is presented which indicates the relative sensitivity of a multiple sensor transducer of this invention, embodied in the specific form described above. The relative sensitivities shown represent the relative magnitudes of the electrical output signals measured across the secondary of a corresponding isolation transformer. Though the sensitivity varies slightly with the direction from which the waves arrive at the transducer, the transducer is substantially omnidirectional in its response, that is, it is substantially equally sensitive to transverse surface waves regardless of the direction of arrival. Of course, if all of the sensor elements were arranged on a single line instead of in a circle, this would not be the case. The omnidirectional properties of this invention may be achieved in varying degrees depending upon the number of sensor elements employed, so long as there are at least three and they are distributed over an area rather than along a single straight line. Some advantage may also be obtained in accordance with this invention even though the sensor elements are not uniformly spaced from each other.

Acoustic emission signals generally occur as a burst, or transient, signal including a number of sinusoidal-like pulses. The burst, or train, of acoustic emission signals include frequency components that lie within the band of frequencies at which maximum response occurs as indicated, for example, in FIG. 7. The acoustic emission transducer that is described above is underdamped. As a result, when such a transient signal arrives at a transducer it excites the individual sensor elements, producing a signal across the output of each element that manifests a ringing effect. Inasmuch as the acoustic emission signals arrive at points of the wall W at different times that depend upon the speed of travel of the wave in the wall, they excite the individual sensors at different times.

As a result of the combined effect, the maximum output occurs at a frequency near the resonant frequency of the array. Maximum combined effect is achieved by establishing the radius of the array to produce a resonant wavelength $\lambda_m$ at a frequency near the resonant frequencies of the individual transducers. In this way, the combined ringing effects have a maximum response at a frequency near the frequency to which the transducer has been tuned, as explained above. In effect, the radius of the array is made about equal to the wavelength that corresponds to resonant frequencies of the individual sensor elements.

By means of this invention, acoustic emission signals existing in the form of transverse surface waves are preferentially detected, thereby improving the reliability of measurements for determining the location and strength of sources of acoustic emission signals.

The invention claimed is:

1. In an acoustic emission transducer for detecting high frequency transverse components of vibrations traveling along the surface of an object that emits acoustic emission signals from parts thereof, the combination of:
a base plate attachable to said surface;
a plurality of electromechanical sensor elements mounted on said base plate and selectively responsive to vibrations normal to said base plate, each said sensor comprising at least one piezoelectric member and being adapted to produce electrical signals at its output corresponding to forces acting on said sensors in a direction normal to said base plate;
a plurality of adjustable means secured relative to said base plate for adjustably compressing said sensor elements against said plate; and
means for interconnecting the electrical outputs of said sensors to combine the electrical signals produced by them.

2. An improved acoustic emission detector as defined in claim 1 having at least three such sensor elements, wherein said sensor elements are arranged in a circle and have equal sensitivities and in which the diameter of the circle is about equal to the wavelength of transverse components of acoustic emission signals that travel along the surface of said body in the range of frequencies characteristic of transverse acoustic emission surface waves.

3. An improved acoustic emission detector as defined in claim 2, wherein each said sensor element comprises at least one piezoelectric crystal disc having its axis of sensitivity normal to said base plate.

4. An improved acoustic emission detector as defined in claim 3, wherein the spacing and arrangement of the sensor elements on said base plate and the electrical interconnections between their outputs are such that the combined electrical signals have their maximum sensitivity in the high frequency range of transverse acoustic emission signals between about 100 kHz and about 1200 kHz and the radial resonant frequencies of said disc also lie in said high frequency range.

5. An improved acoustic emission transducer as defined in claim 1, comprising at least three sensor elements, each of which includes at least one piezoelectric crystal disc respectively, arranged in a nonlinear array on said base plate with the sensitive axes of the piezoelectric discs normal to said base plate, the spacing and arrangement of the crystal discs on the base plate being such that the transducer is tuned to a frequency near the center of the high frequency range between about 100 kHz and about 1200 kHz and the radial resonant frequency of said crystal discs in a direction transverse to the sensitive axes thereof lie in said range and differ from said first mentioned resonant frequency between about ±10% and about ±20%.

6. An improved acoustic emission transducer as defined in claim 5, wherein said resonant frequencies are about 400 kHz.

7. An improved acoustic emission detector as defined in claim 3, wherein each said sensor element is in the form of a plurality of piezoelectric crystals of annular configuration with the end surfaces of the annuli parallel to said surface.

8. An acoustic emission transducer for detecting components of high frequency transverse vibrations traveling along the surface of an object that emits acoustic emission signals from parts thereof, the combination of:
a base plate attachable to said surface;
a support plate secured to and spaced from said base plate, said support plate having a plurality of threaded bores that have their axes parallel to a central axis that extends through said base plate and are arranged in a circle about said central axis;
a plurality of at least three electromechanical sensor elements mounted in a nonlinear array on said base plate and selectively responsive to vibrations normal to said base plate, each said sensor comprising at least one piezoelectric member having its sensitive axis parallel to said central axis, said piezoelectric elements having central axes aligned with the axes of said bores, each said sensor being adapted to produce electrical signals at its output corresponding to forces acting on said sensors in a direction normal to said base plate;
means including screws threadibly engaging said bores for adjustably compressing said sensor elements between said base plate and said support plate; and
means for interconnecting the electrical outputs of said sensor elements to combine the electrical signals produced by them.

9. An improved acoustic emission detector as defined in claim 8, wherein said sensor elements have equal sensitivities and said elements are uniformly spaced about said circle, and the diameter of the circle is about equal to the wavelength of transverse acoustic emission signals that travel along the surface of said body.

10. An acoustic emission transducer for detecting transverse components of high frequency vibrations traveling along the surface of an object that emits acoustic emission signals from parts thereof, the combination of:
a base plate attachable to said surface;
a plurality of at least three electromechanical sensor elements mounted in a nonlinear array on said base plate and selectively responsive to vibrations normal to said base plate, each said sensor element being adapted to produce electrical signals at its output corresponding to forces acting on said sensor element in a direction normal to said base plate; and
means for interconnecting the electrical outputs of said sensor elements to combine the electrical signals produced by them;
the spacing and arrangement of the sensors on the base plate and the electrical interconnections between their outputs and the characteristics of the sensors being such that the combined electrical signals have their maximum sensitivity in the high frequency range of transverse acoustic emission signals between about 300 kHz and about 600 kHz.

11. An improved acoustic emission detector as defined in claim 10 wherein said sensor elements are arranged in a circle and have equal sensitivities and in which the radius of the circle is about equal to the wavelength of transverse acoustic emission signals that travel along the surface of said body in said frequency range.

12. An improved acoustic emission detector as defined in claim 11 in which the radial resonant frequency at which said sensor elements have their respective maximum sensitivity lies in said frequency range.

13. An improved acoustic emission detector as defined in claim 10 wherein each said sensor element comprises a piezoelectric crystal of annular configuration with the end surfaces of the annuli parallel to the surface of said base plate.

14. An acoustic emission transducer for detecting transverse components of high frequency vibrations traveling along the surface of an object that emits acoustic emission signals from parts thereof, the combination of:
   a base plate attachable to said surface;
   a plurality of at least three electromechanical sensor elements mounted in a nonlinear array on said base plate and selectively responsive to vibrations normal to said base plate, each said sensor element being adapted to produce electrical signals at its output corresponding to forces acting on said sensor element in a direction normal to said base plate, each of said sensor elements producing a ringing effect in a predetermined frequency range between about 300 kHz and about 600 kHz;
   means for interconnecting the electrical outputs of said sensor elements to combine the electrical signals produced by them;
   the spacing and arrangement of the sensors on the base plate and the electrical interconnections between their outputs such that when a transient acoustic emission signal traveling along the surface is detected by the sensor elements the combined electrical ringing signals have their maximum amplitude in said high frequency range.

15. An improved acoustic emission detector as defined in claim 14 wherein said sensor elements are arranged in a circle and have equal sensitivities and in which the diameter of the circle is about equal to the wavelength of acoustic emission signals of such predetermined frequency that travel along the surface of said body.

* * * * *